United States Patent
Suenger et al.

(10) Patent No.: US 8,137,412 B2
(45) Date of Patent: Mar. 20, 2012

(54) BLEACHING WITH CONCOMITANT HAIR TONICIZING

(75) Inventors: Georg Suenger, Duesseldorf (DE); Wibke Gross, Hueckelhoven (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/156,482

(22) Filed: Jun. 9, 2011

(65) Prior Publication Data

US 2011/0232669 A1    Sep. 29, 2011

Related U.S. Application Data

(63) Continuation of application No. PCT/EP2009/066610, filed on Dec. 8, 2009.

(30) Foreign Application Priority Data

Dec. 11, 2008  (DE) .......................... 10 2008 061 133

(51) Int. Cl.
*D06L 3/00* (2006.01)

(52) U.S. Cl. .................... 8/101; 8/107; 8/109; 8/111

(58) Field of Classification Search .............. 8/101, 107, 8/109, 111
See application file for complete search history.

(56) References Cited

U.S. PATENT DOCUMENTS

| | | | |
|---|---|---|---|
| 7,981,166 B2 * | 7/2011 | Gross et al. | 8/101 |
| 8,034,122 B2 * | 10/2011 | Gross et al. | 8/101 |
| 2003/0077237 A1 | 4/2003 | Legrand et al. | |
| 2005/0262647 A1 | 12/2005 | Hoeffkes et al. | |
| 2011/0047712 A1 | 3/2011 | Gross et al. | |

FOREIGN PATENT DOCUMENTS

| | | |
|---|---|---|
| DE | 10148845 A1 | 4/2003 |
| DE | 10315421 A1 | 10/2004 |
| DE | 102006041292 A2 | 3/2008 |
| DE | 102007047685 A1 * | 7/2008 |
| EP | 0998908 A2 | 5/2000 |
| EP | 1721598 A1 | 11/2006 |
| WO | 2006036747 A2 | 4/2006 |
| WO | 2010130513 A2 | 11/2010 |

OTHER PUBLICATIONS

Schrader, Karlheinz. Grundlagen und Rezepturen der Kosmetika (Fundamentals and Formulations of Cosmetics), 2, Hëthig Buch Verlag GmbH, Heidelberg 1989.

Umbach, W. Kosmetik Entwicklung, Herstellung und Anwendung kosmetischer Mittel, Georg Thieme Verlag, 1995.

Römp-Lexikon. Lexicon of Chemistry. George Thieme Verlag, vol. 10, 1997, p. 1764.

* cited by examiner

*Primary Examiner* — Eisa Elhilo
(74) *Attorney, Agent, or Firm* — David P. LeCroy

(57) ABSTRACT

Bleaching method for keratin fibers, using an agent comprising a bleach activator system comprising at least one cationic acylpyridinium derivative of formula (I), and hydrogen peroxide and use of agents for bleaching keratin fibers, in particular human hair, comprising at least one cationic acylpyridinium derivative, for reinforcing the bleaching capacity with concomitant improvement in the condition of the fibers.

8 Claims, No Drawings

BLEACHING WITH CONCOMITANT HAIR TONICIZING

CROSS REFERENCE TO RELATED APPLICATIONS

The present application is a continuation of International Application No. PCT/EP2009/066610 filed 8 Dec. 2009, which claims priority to German Patent Application No. 10 2008 061 133.6 filed 11 Dec. 2008, both of which are incorporated herein by reference.

The present invention relates to the use of agents for bleaching keratinous fibers, particularly human hair, containing a bleach activator system comprising at least one cationic acyl pyridinium derivative and hydrogen peroxide to enhance the bleaching performance while at the same time improving the condition of the fibers.

Modifying the shape and color of hair is an important area of modern cosmetics. Through modification, the hair's appearance can be adapted both to current fashion trends and to a person's individual wishes. Permanent waves and other methods for modifying hair shape can be applied to nearly all types of hair treated. In contrast, dyeing and blonding methods are restricted to specific initial hair colors. Blonding methods are known to a person skilled in the art and may be looked up in relevant monographs such as Kh. Schrader, Grundlagen and Rezepturen der Kosmetika, 2nd Ed. 1989, Dr. Alfred Hüthig Verlag, Heidelberg, or W. Limbach (ed.), Kosmetik, 2nd Ed. 1995, Georg Thieme Verlag, Stuttgart, New York.

In addition to dyeing, bleaching or blonding of natural hair color is desired by many consumers, since blonde hair color is considered attractive and desirable from a fashion standpoint. A variety of blonding agents with varying blonding performance are commercially available for this purpose. Oxidizing agents contained in these products are able to bleach hair fibers by oxidative destruction of the hair's own melanin dye. For a moderate blonding effect, it is sufficient to use hydrogen peroxide as the sole oxidizing agent, optionally together with ammonia or other alkalizing agents. To achieve a stronger blonding effect, a mixture of hydrogen peroxide and peroxodisulfate salts and/or peroxomonosulfate salts is commonly used. However, bleaching is also accompanied by hair damage as it is not only the natural color-imparting components of the hair that suffer oxidative damage, but also other structural components of the hair. Depending on how pronounced the degree of damage is, this ranges from hair that is rough, brittle and more difficult to comb, through reduced resistance and tensile strength of the hair, to hair breakage. The greater the amount of hydrogen peroxide and optionally peroxodisulfates used, the more severe the damage caused to the keratin fibers will generally be. In particular splitting or even breaking of the fibers, which can occur particularly when the blonding process is repeated several times, are side effects of blonding that are highly undesirable for the consumer. Hair dyes or bleaching agents having good bleaching performance without simultaneously damaging the hair fibers are hitherto unknown. Bleaching agents which, in addition to increased bleaching performance, make a positive contribution to improving fiber structure, and thus simultaneously act as treatment or conditioning agents, are especially desirable.

Before being applied onto human hair, hair dyes and/or bleaching agents in solid or pasty form are commonly mixed with a dilute aqueous hydrogen peroxide solution. This mixture is then applied onto the hair and rinsed out again after a specific exposure time. Exposure time on the hair needed to achieve complete decolorization or bleaching is from about 30 to 40 minutes. There is a desire among users of these hair dyes or blonding agents to shorten this exposure time.

Blonding processes on keratinous fibers generally take place at alkaline pH, particularly from 9.0 to 10.5. These pH values are required to ensure that the external cuticle (cuticula) opens up, thereby allowing active species (dye precursors and/or hydrogen peroxide) to penetrate into the hair. Ammonia is commonly used as an alkalizing agent, but this is disadvantageous due to its intense odor and possible irritation, which may go as far as causing skin irritation and skin sensitization.

Even if presently available blonding agents generally display good bleaching performance, they tend not to be regarded as ideal due to long application times and hair damage that results from the high concentrations of oxidizing and alkalizing agents.

In the past, attempts to incorporate commercial conditioners into bleaching agents have often proved inadequate and unsuccessful, since conventional conditioners for keratinous fibers lack stability, particularly under the harsh conditions of blonding, and only display limited effectiveness. Thus, a great need still exists to improve these conditioning bleaching agents.

There has been no lack of attempts to minimize the hair damage associated with blonding, without having to accept losses of bleaching performance in the agents. Thus, WO2006/036747 A2 relates to coloring and bleaching agents with special radical scavengers and precursors of peroxymonocarbonate ions to reduce damage to hair fibers.

The use of cationic acyl pyridinium derivatives in hair dyeing is known, for example, from the documents DE 10148845 A1 or DE 10261656 A1. In both documents, however, these derivatives are described together with at least a second dyeing component as an agent for dyeing, and thus for increasing the color intensity of the hair. It has not been apparent from the prior art that a bleach activator system having at least one cationic acyl pyridinium derivative and hydrogen peroxide can be used for enhanced bleaching of hair with simultaneous hair fiber protection or even improvement of the fiber structure.

The present invention therefore provides methods for bleaching or blonding hair which, in addition to improved bleaching performance, exhibit reduced hair damage as well as strengthen the fiber structure and thus improve the condition of the hair.

Unpredictably, it has now been found that the use of a bleach activator system comprising at least one cationic acyl pyridinium derivative in combination with hydrogen peroxide bleaches the hair much more strongly than possible by use of a comparable quantity of hydrogen peroxide alone, while at the same time significantly strengthening the fiber structure and conditioning the hair with a lasting effect.

A method for bleaching keratinous fibers is provided, in which a bleaching agent is applied on to the keratin-containing fibers, left on the fibers for an exposure time of 1 to 30 minutes, and then rinsed out or washed out with a shampoo. The bleaching agent contains in a cosmetic carrier, in addition to hydrogen peroxide, at least one cationic acyl pyridinium derivative of formula (I),

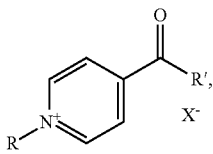

(I)

wherein
R is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a $C_1$-$C_6$ dialkylamino $C_2$-$C_6$ alkyl group, a heteroaryl $C_1$-$C_6$ alkyl group, a 3-oxobutyl group, a 2-oxopropyl group, an aryl group or a heteroaryl group, R' is a $C_1$-$C_4$ alkyl group, a $C_2$-$C_6$ hydroxyalkyl group or a $C_1$-$C_6$ alkoxy $C_2$-$C_6$ alkyl group, and $X^-$ is a physiologically acceptable anion.

Keratinous fibers, or also keratin fibers, refer to fur, wool, feathers and particularly human hair. Although agents according to the invention are primarily suitable for dyeing and/or bleaching keratin fibers, they can also be used in other fields.

Examples of the residues mentioned as substituents for compounds of formula (I) are listed below:

Examples of $C_1$-$C_6$ alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$.

Examples of a $C_2$-$C_6$ alkenyl group are a prop-2-enyl group (allyl group), a 2-methylprop-2-enyl group, a but-3-enyl group, a but-2-enyl group, a pent-4-enyl group or a pent-3-enyl group. The prop-2-enyl group is particularly preferred in this context.

Other preferred examples of a $C_2$-$C_6$ hydroxyalkyl group that can be used are —$CH_2CH_2OH$, —$CH_2CH_2CH_2OH$, —$CH_2CH(OH)CH_3$, —$CH_2CH_2CH_2CH_2OH$, with the group —$CH_2CH_2OH$ being preferred.

Examples of $C_1$-$C_6$ alkoxy $C_2$-$C_6$ alkyl groups are —$CH_2CH_2OCH_3$, —$CH_2CH_2CH_2OCH_3$, —$CH_2CH_2OCH_2CH_3$, —$CH_2CH_2CH_2OCH_2CH_3$, —$CH_2CH_2OCH(CH_3)_2$, and —$CH_2CH_2CH_2OCH(CH_3)_2$.

Examples of a carboxy $C_1$-$C_6$ alkyl group are the carboxymethyl group, the 2-carboxyethyl group or the 3-carboxypropyl group.

Examples of aryl $C_1$-$C_6$ alkyl groups are the benzyl group and the 2-phenylethyl group.

Examples of a heteroaryl $C_1$-$C_6$ alkyl group are the pyridin-2-ylmethyl group, the pyridin-3-ylmethyl group, the pyridin-4-ylmethyl group, the pyrimidin-2-ylmethyl group, the pyrrol-1-ylmethyl group, the pyrrol-1-ylethyl group, the pyrazol-1-ylmethyl group or the pyrazol-1-ylethyl group.

Examples of a mono- or di-$C_1$-$C_6$-alkylamino $C_2$-$C_6$ alkyl group are the 2-methylaminoethyl group, 2-ethylaminoethyl group, 2-dimethylaminoethyl group, 2-diethylaminoethyl group, 3-methylaminopropyl group, 3-dimethylaminopropyl group, 1-piperidinoethyl group, 1pyrrolidinoethyl group, 4-morpholinoethyl group and 2-bis(2-hydroxyethyl)aminoethyl group, with the 2-dimethylaminoethyl group and the 2-diethylaminoethyl group being particularly preferred.

An example of an aryl group is the phenyl group, the 1-naphthyl group or the 2-naphthyl group.

Examples of a heteroaryl group are the pyridin-2-yl group, the pyridin-3-yl group, the pyridin-4-yl group, the pyrimidin-2-yl group, the pyrrol-1-yl group, the pyrrol-2-yl group, the pyrazol-1-yl group, the pyrazol-3-yl group or the pyrazol-2-yl group.

Useful bleaching agents contain at least two essential components: at least one cationic acyl pyridinium derivative of formula (I), and hydrogen peroxide. Agents according to the invention can also be "application mixtures" (i.e., agents which, although packaged separately (e.g., for reasons of stability), are mixed together prior to application to form an application mixture and then applied).

Compounds according to formula (I) are preferably suitable if the residue R of general structure (I) is a $C_1$-$C_6$ alkyl group, a $C_2$-$C_6$ alkenyl group or a $C_2$-$C_6$ hydroxyalkyl group. It is furthermore preferred according to the invention for R' of formula (I) to represent a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, particularly a $C_1$-$C_6$ alkyl group (preferably methyl, ethyl, n-propyl or isopropyl).

Preferably the anion $X^-$ according to formula (I) is chosen from halide, particularly chloride, bromide and iodide, benzenesulfonate, p-toluenesulfonate, $C_1$-$C_4$ alkyl sulfonate, trifluoromethane sulfonate, acetate, trifluoroacetate, perchlorate, 1/2 sulfate, hydrogen sulfate, tetrafluoroborate, hexafluorophosphate or tetrachlorozincate. Particularly favorably according to the invention, the physiologically acceptable anion $X^-$ is a halide ion (particularly chloride or bromide), hydrogen sulfate, 1/2 sulfate, p-toluenesulfonate, benzenesulfonate or acetate.

Particularly preferred cationic acyl pyridinium derivatives of general formula (I) are salts of 4-acetyl-1-methylpyridinium, 4-acetyl-1-allylpyridinium, 4-acetyl-1-(2-hydroxyethyl)pyridinium, 4-acetyl-1-(2-oxopropyl)pyridinium, 4-acetyl-1-ethylpyridinium, 4-acetyl-1-(2-methylprop-2-enyl)pyridinium, 4-acetyl-1-benzylpyridinium and 4-acetyl-1-(2-methoxyethyl)pyridinium.

In summary, preferred agents contain as cationic acyl pyridinium derivative of general structure (I) at least one compound from the group of 4-acetyl-1-methylpyridinium p-toluenesulfonate, 4-acetyl-1-methylpyridinium benzenesulfonate, 4-acetyl-1-methylpyridinium bromide, 4-acetyl-1-methylpyridinium hydrogen sulfate, 4-acetyl-1-allylpyridinium p-toluenesulfonate, 4-acetyl-1-allylpyridinium benzenesulfonate, 4-acetyl-1-allylpyridinium bromide, 4-acetyl-1-allylpyridinium hydrogen sulfate, 4-acetyl-1-(2-hydroxyethyl)pyridinium p-toluenesulfonate, 4-acetyl-1-(2-hydroxyethyl)-pyridinium benzenesulfonate, 4-acetyl-1-(2-hydroxyethyl)pyridinium bromide, 4-acetyl-1-(2-hydroxyethyl)pyridinium hydrogen sulfate, 4-acetyl-1-(2-oxopropyl)pyridinium p-toluenesulfonate, 4-acetyl-1-(2-oxopropyl)pyridinium benzenesulfonate, 4-acetyl-1-(2-oxopropyl)pyridinium bromide, 4-acetyl-1-(2-oxopropyl)pyridinium hydrogen sulfate, 4-acetyl-1-ethylpyridinium p-toluenesulfonate, 4-acetyl-1-ethylpyridinium benzenesulfonate, 4-acetyl-1-ethylpyridinium bromide, 4-acetyl-1-ethylpyridinium hydrogen sulfate, 4-acetyl-1-(2-methylprop-2-enyl)pyridinium p-toluenesulfonate, 4-acetyl-1-(2-methylprop-2-enyl)pyridinium benzenesulfonate, 4-acetyl-1-(2-methylprop-2-enyl)pyridinium bromide, 4-acetyl-1-(2-methylprop-2-enyl)pyridinium hydrogen sulfate, 4-acetyl-1-benzylpyridinium p-toluenesulfonate, 4-acetyl-1-benzylpyridinium benzenesulfonate, 4-acetyl-1-benzylpyridinium bromide, 4-acetyl-1-benzylpyridinium hydrogen sulfate, 4-acetyl-1-(2-methoxyethyl)pyridinium p-toluenesulfonate, 4-acetyl-1-(2-methoxyethyl)pyridinium benzenesulfonate, 4-acetyl-1-(2-methoxyethyl)pyridinium bromide and 4-acetyl-1-(2-methoxyethyl)pyridinium hydrogen sulfate. From this group, the following acetyl pyridinium salts are explicitly most particularly preferred: 4-acetyl-1-methylpyridinium p-toluenesulfonate; 4-acetyl-1-methylpyridinium benzenesulfonate; 4-acetyl-1-methylpyridinium bromide; 4-acetyl-1-methylpyridinium hydrogen sulfate; 4-acetyl-1-allylpyridinium p-toluenesulfonate; 4-acetyl-1-allylpyridinium benzenesulfonate; 4-acetyl-1-allylpyridinium bromide; 4-acetyl-1-allylpyridinium hydrogen sulfate; 4-acetyl-1-(2-hydroxyethyl)pyridinium p-toluenesulfonate; 4-acetyl-1-(2-hydroxyethyl)pyridinium benzenesulfonate; 4-acetyl-1-(2-hydroxyethyl)pyridinium bromide and 4-acetyl-1-(2-hydroxyethyl)pyridinium hydrogen sulfate.

Unless explicitly stated otherwise, all quantities mentioned below refer to total weight of the ready-to-use agent.

Agents according to the invention contain as a first essential ingredient acyl pyridinium derivatives of the general structure (I), preferably in an amount of 0.01 to 25 wt. %, particularly 0.1 to 10 wt. %, based on total weight of the ready-to-use agent.

As a second essential ingredient, the bleaching agent used in the method according to the invention contains hydrogen peroxide. Hydrogen peroxide is preferably used as an aqueous solution. However, hydrogen peroxide can also be used in the form of a solid addition compound of hydrogen peroxide to inorganic or organic compounds, such as sodium perborate, sodium percarbonate, magnesium percarbonate, sodium percarbamide, polyvinylpyrrolidinone n $H_2O_2$ (n is a positive integer greater than 0), urea peroxide and melamine peroxide. In the last-mentioned case, the addition compounds in the application mixture according to the invention release hydrogen peroxide (i.e., these agents contain free hydrogen peroxide as well as the addition compound in the cosmetic carrier).

Most particularly preferably according to the invention, the hydrogen peroxide is added to the agent according to the invention as an aqueous hydrogen peroxide solution. The concentration of a hydrogen peroxide solution is determined by legal guidelines and by the desired effect. Preferably 6 to 12 wt. % solutions in water are used. Preferred agents according to the invention contain—based on their total weight—0.01 to 12 wt. %, preferably 0.1 to 10 wt. %, particularly preferably 1 to 6 wt. % hydrogen peroxide (calculated as 100% $H_2O_2$).

It has been demonstrated that the adjustment of the desired rheological properties of the agent in the method according to the invention with the aid of associative polymers leads to particularly advantageous results in terms of hair conditioning. Within the framework of the invention, associative polymers refer to water-soluble polymers which form reversible, ordered structures with one another or with other additives in an aqueous medium and thus are able to have a decisive influence on the viscosity and other rheological properties of the agent.

Associative polymers generally comprise hydrophilic and hydrophobic sections in their structure, the hydrophobic properties caused structurally by the presence of a fatty alkyl chain. The term "fatty alkyl chain" is a linear or branched alkyl chain, which is optionally unsaturated and/or substituted with halogen atoms or hydroxy groups, consists of 6 to 30, preferably 8 to 22 C atoms.

One particular embodiment of the present invention is wherein the agent additionally contains at least one associative polymer.

Suitable associative polymers according to the invention are anionic, cationic, amphoteric or nonionic polymers.

Suitable anionic associative polymers according to the invention are preferably copolymers of ethylenically unsaturated acids as monomers for the hydrophilic, anionic structural element and another olefinic monomer containing the fatty alkyl chain.

Suitable ethylenically unsaturated acids include in particular acrylic acid, methacrylic acid, maleic anhydride, crotonic acid and itaconic acid. Acrylic acid and methacrylic acid are particularly preferred.

As the olefinic monomer which contains the fatty alkyl chain, monomers according to the formula (MF) are preferably used according to the invention,

$$CH_2=CR-X-R' \tag{MF}$$

wherein R is hydrogen or a methyl group,
R' is an alkyl chain with 6 to 30, preferably 8 to 22 C atoms which is linear or branched, optionally unsaturated and/or substituted with halogen atoms or hydroxy groups, and
X is a methylene oxy group —$CH_2O$—, an ethoxylated methylene oxy group —$CH_2O(CH_2CH_2O)_n$—, a carboxyl group —$C(=O)O$—, an ethoxylated carboxyl group —$C(=O)O(CH_2CH_2O)_n$— or an oxycarbonyl group —$OC(=O)$—, where n is an integer from 1 to 100, preferably 1 to 25.
R' preferably is a linear or branched $C_9$-$C_{22}$ group.

Examples of preferred anionic associative polymers according to the invention are:
a) Copolymers of acrylic acid and/or methacrylic acid and ethoxylated allyl ethers according to formula (MF), where R is hydrogen and X is an ethoxylated methylene oxy group —$CH_2O(CH_2CH_2O)_n$— with n as an integer from 5 to 25, and optionally other monomers. Explicit examples of such polymers are terpolymers of methacrylic acid, steareth-10 allyl ether and ethyl acrylate and are marketed under the trade name Salcare 80 or Salcare 90.
b) Copolymers of acrylic acid and/or methacrylic acid together with alkyl acrylates according to formula (MF), where R is hydrogen and X is a carboxyl group —$C(=O)O$—, and optionally other monomers. Explicit examples of such polymers are copolymers of acrylic acid and $C_{10}$-$C_{30}$ alkyl acrylates and are marketed under the trade names Pemulen TR1, Pemulen TR2, Carbopol ETD 2020, Carbopol Ultrez 20 or Carbopol 1382, as well as polymers which, in addition to acrylic acid, lauryl acrylate and stearyl acrylate, also contain N-oxo-N,N-dimethylaminoethyl methacrylate as monomer (trade names Diaformer Z-711, Z-712, Z-731 and Z-651).
c) Copolymers of acrylic acid and/or methacrylic acid together with vinyl alkyl esters according to formula (MF), where R is hydrogen and X is an oxycarbonyl group —$OC(=O)$—, and optionally other monomers. Explicit examples of such polymers are copolymers of acrylic acid and vinyl isodecanoate or vinyl neodecanoate and are marketed under the trade names Stabylen 30 and Aculyn 38.
d) Copolymers of acrylic acid and/or methacrylic acid together with alkyl acrylates according to formula (MF), where R is hydrogen and X is an ethoxylated carboxyl group —$C(=O)O(CH_2CH_2O)_n$—, and optionally other monomers. Explicit examples of such polymers are copolymers of acrylic acid and beheneth-25 methacrylate (trade name Aculyn 28), the terpolymer of methacrylic acid, steareth-20 methacrylate and ethyl acrylate (trade name Aculyn 22) and the copolymer of methacrylic acid and steareth-20 methacrylate (trade name Aculyn 88 or Structure 2001 and Structure 3001).

Particularly preferred anionic associative polymers according to the invention are copolymers of acrylic acid and/or methacrylic acid and vinyl alkyl esters according to formula (MF), where R is hydrogen, X is an oxycarbonyl group —OC(=O)— and R' is a linear or branched $C_9$-$C_{17}$ alkyl chain, particularly a branched $C_9$ alkyl chain, and optionally other monomers.

Suitable cationic associative polymers include:
a) cationized polyurethanes,
b) copolymers with cationic acrylic acid esters/amides which also contain a fatty chain, and
c) cationic cellulose derivatives, particularly hydroxyethyl cellulose derivatives with alkyl chains.

Examples of cationic associative polymers of type b) are the terpolymer 3-(N-dodecyl-N,N-dimethylammonio)propyl methacrylamide chloride, 3-(N,N-dimethylamino)propyl methacrylamide and N-vinylpyrrolidinone with the INCI name Polyquaternium-55 (trade names Styleze W10/Styleze W20) and the tetrapolymer 3-(N-dodecyl-N,N-dimethylammonio)propyl methacrylamide chloride, 3-(N,N-dimethylamino)propyl methacrylamide, N-vinylpyrrolidinone and N-vinylcaprolactam with the INCI name Polyquaternium-69 (trade name Aquastyle 300).

Examples of cationic associative polymers of type c) are quaternized $C_8$-$C_{30}$ alkyl hydroxyethyl celluloses, such as products with the trade names Quatrisoft LM200 and Quatrisoft LM-X 529, as well as Crodacel QM, Crodacel QL and Crodacel QS.

Preferred amphoteric associative polymers are copolymers of ethylenically unsaturated acids as monomers for the hydrophilic anionic structural element and another cationic, olefinic monomer, where the fatty alkyl chain can be found structurally either in the cationic monomer or in an additional monomer.

Preferred nonionic associative polymers are fatty alkyl chain-containing celluloses/cellulose derivatives, fatty alkyl chain-containing hydroxypropyl guar gums, copolymers of N-vinylpyrrolidinone with fatty alkenes (such as eicosene or hexadecene), copolymers of $C_1$-$C_4$ alkyl (meth)acrylates and (meth)acrylic acid esters of ethoxylated fatty alcohols (such as copolymers of methyl acrylate and steareth acrylate), copolymers of ethoxylated (meth)acrylic acid and $C_8$-$C_{30}$ alkyl (meth)acrylates and polyurethanes with hydrophobic and hydrophilic structural sections.

Particularly preferred nonionic associative polymers are polyurethanes wherein the hydrophobic and hydrophilic structural sections are present as blocks, for example, with a central hydrophilic unit and hydrophobic end regions. The hydrophilic region is formed structurally preferably by polyethylene oxide sections. Most particularly preferred nonionic associative polymers are represented by polyurethanes obtainable from the reaction of PEG-150 to PEG-180 and methylene bis(4-cyclohexyl isocyanate) with decyl alcohol (trade name Aculyn 44) or with stearyl alcohol (trade name Aculyn 46).

Preferably, the agent contains the associative polymer or polymers in an amount of 0.005 to 3 wt. %, preferably 0.01 to 1.5 wt. %, based on total weight of the ready-to-use agent.

It has been demonstrated that the conditioning effect in the method according to the invention can be significantly increased if the bleaching agent additionally contains at least one dialkyl ether and/or dialkyl carbonate. One particular embodiment of the present invention is therefore a method wherein the bleaching agent additionally contains at least one dialkyl ether and/or dialkyl carbonate.

Preferred dialkyl ethers according to the invention are given by the formula R—O—R', where R and R', each independently of one another, are a linear or branched $C_6$-$C_{25}$ alkyl. In one preferred embodiment, R and R' are the same. Examples of preferred dialkyl ethers according to the invention are di-n-hexyl ether, di-n-heptyl ether, di-n-octyl ether, di-n-nonyl ether, di-n-decyl ether, di-isodecyl ether, di-n-dodecyl ether, di-n-tetradecyl ether, di-n-hexadecyl ether and di-n-octadecyl ether. Most particularly preferred is di-n-octyl ether (INCI name: Dicarylyl ether), marketed, for example, with the trade names Cetiol OE or Rofetan OE.

Preferred dialkyl carbonates according to the invention are illustrated by the formula R—OC(=O)O—R', where R and R', each independently of one another, are a linear or branched $C_6$-$C_{25}$ alkyl chain. In one preferred embodiment, R and R' are the same. Preferred dialkyl carbonates include di-n-hexyl carbonate, di-n-heptyl carbonate, di-n-octyl carbonate, di-n-nonyl carbonate, di-n-decyl carbonate, di-isodecyl carbonate, di-n-dodecyl carbonate, di-n-tetradecyl carbonate, di-n-hexadecyl carbonate and di-n-octadecyl carbonate. Most particularly preferred are di-n-octyl carbonate (INCI name: Dicarylyl carbonate; trade name Cetiol CC) and di-3-octyl carbonate (INCI name: Dicarylyl carbonate; trade name Tegosoft DEC). According to the invention, the agent preferably contains dialkyl ethers and/or dialkyl carbonates in an amount of 0.05 to 10 wt. %, preferably 0.1 to 5 wt. %, based on total weight of the ready-to-use agent.

In a preferred embodiment of the method according to the invention, the agent contains as an additional ingredient at least [one] co-bleach activator and/or the physiologically acceptable salt thereof.

This co-bleach activator is preferably chosen from aliphatic and/or carbocyclic co-bleach activators. This co-bleach activator particularly preferably contains as an essential structural feature a hydroxyl group, a carboxylic acid, a sulfuric acid monoester, a phosphoric acid monoester and/or a physiologically acceptable salt thereof. If the toxicologically harmless co-bleach activator contains a structural unit which allows a plurality of spatial arrangements, such as substituted double bonds or centers of asymmetry, all possible stereoisomers are of course included within the framework of the present invention. However, it may optionally also be preferred to use either just one possible stereoisomer or a mixture of two or more stereoisomers.

Preferred agents according to the invention contain as co-bleach activator and/or the physiologically acceptable salt thereof at least one co-bleach activator according to formula (II) and/or the physiologically acceptable salt thereof,

(II)

wherein
Y is a carbonyl group, a direct bond or methylene group;
R1 is hydrogen, a $C_1$-$C_4$ alkyl group, a physiologically acceptable cation or an $SO_3^-$ or a $PO_3^{2-}$ group;
R2 is an amino group, a methylamino group, a dimethylamino group, a trimethylammonio group, phenyl, benzyl, phenoxymethyl, 1-naphthyl, 2-naphthyl, 2-, 3-, 4-toluoyl, or an R4-O—$(CH_2CH_2O)_n$ group, where R4 denotes a $C_6$-$C_{20}$ alkyl group and n is a number greater than 15;
R3 is hydrogen or an optionally branched $C_1$-$C_6$ alkyl group;
with the proviso that
    if Y is a carbonyl group,
    R1 is hydrogen, a $C_1$-$C_4$ alkyl group or a physiologically acceptable cation, R2 is an amino group, a methylamino group, a dimethylamino group or a trimethylammonio group, and R3 is hydrogen or an optionally branched $C_1$-$C_6$ alkyl group, if Y is a direct bond, R1 is hydrogen, R2 is phenyl, benzyl, phenoxymethyl, 1-naphthyl, 2-naphthyl, 2-, 3- or 4-toluoyl, and R3 is hydrogen or an optionally branched $C_1$-$C_6$ alkyl group, and if Y is a methylene group, R1 is an $SO_3^-$ or a $PO_3^{2-}$ group, R2 is an $R4$-$O(CH_2CH_2O)_n$ group, where R4 is a $C_6$-$C_{20}$ alkyl group and n is a number greater than 15, and R3 is hydrogen.

Preferred agents according to the invention contain at least one aliphatic amino acid, optionally N-methylated or N,N-dimethylated on the nitrogen atom thereof, and/or the physiologically acceptable salt thereof as co-bleach activator. Amino acids generally contain in their structure asymmetric centers, particularly carbon atoms, as centers of chirality. Within the framework of the present invention, amino acids can be used as pure chiral substances or as mixtures of enantiomers and/or diastereomers. In particular, racemic mixtures (i.e., mixtures in which both enantiomers of a compound are contained in equal proportions) may be preferred. One enantiomeric form usually predominates in nature. It may therefore also be preferred to use amino acids in their naturally occurring or precisely in their unnatural configuration. Preferred co-bleach activators are selected from glycine, N-methyl glycine, N,N-dimethyl glycine, alanine, D/L-alanine, L-alanine, D-alanine, N-methyl alanine, N,N-dimethyl alanine, leucine, D/L-leucine, L-leucine, D-leucine, N-methyl leucine, N,N-dimethyl leucine, isoleucine, D/L-isoleucine, L-isoleucine, D-isoleucine, N-methyl isoleucine, N,N-dimethyl isoleucine or the physiologically acceptable salts thereof. Glycine and/or the physiologically acceptable salt thereof are particularly preferably contained in the agent according to the invention as co-bleach activator.

Preferred agents contain at least one aromatic alcohol and/or the physiologically acceptable salt thereof as co-bleach activator. Benzyl alcohol, 2-phenylethyl alcohol, 1-phenylethyl alcohol, 2-phenoxyethanol, 1-hydroxymethylnaphthalene and/or 2-hydroxymethylnaphthalene may be mentioned as preferred aromatic alcohols. A most particularly preferred aromatic alcohol as co-bleach activator is benzyl alcohol.

Finally, those agents containing as co-bleach activator a physiologically acceptable salt of an alkyl ether sulfate according to formula (III)

$$R4\text{-}O(CH_2CH_2O)_mSO_3Y \qquad (III),$$

wherein R4 is a $C_6$-$C_{20}$ alkyl group, m is a number greater than 15 and Y is an alkali metal and/or alkaline earth metal, ammonium, alkyl ammonium or alkanol ammonium, may be preferred according to the invention.

Alkyl ether sulfates ("ether sulfates") are manufactured on an industrial scale by $SO_3$ or chlorosulfonic acid (CSA) sulfation of fatty or oxo alcohol polyglycol ethers and subsequent neutralization. Examples which are preferred according to the invention are sulfates in the form of the sodium and/or magnesium salts of highly ethoxylated addition products of at least 16, but averaging 20 to 40 and in particular 25 to 35 mol of ethylene oxide (expressed by m in formula (III)) onto caproic alcohol, caprylic alcohol, 2-ethylhexyl alcohol, capric alcohol, lauryl alcohol, isotridecyl alcohol, myristyl alcohol, cetyl alcohol, stearyl alcohol, isostearyl alcohol, eicosyl alcohol or the technical mixtures thereof. These are obtained, for example, in high pressure hydrogenation of technical methyl esters based on fats and oils or aldehydes from Roelen's oxo synthesis and as a monomer fraction in the dimerization of unsaturated fatty alcohols. Preferred are technical fatty alcohols with 12 to 18 carbon atoms, such as coconut, palm, palm kernel or tallow fatty alcohol. Ether sulfates can have both a conventional and a narrow homologue distribution. It is particularly preferred to use ether sulfates based on adducts of on average 25 to 35 mol of ethylene oxide onto technical $C_{12/14}$ or $C_{12/18}$ coconut fatty alcohol fractions in the form of the sodium and/or magnesium salts thereof.

One particularly preferred co-bleach activator is known by the INCI name Sodium Coceth-30 Sulfate and is distributed by Cognis as a 31-33 wt. % aqueous solution under the trade name Disponil FES 77.

The co-bleach activator(s) is/are preferably used within specific quantitative ranges. Agents according to the invention are preferred which have 0.01 to 10 wt. %, particularly 0.1 to 5 wt. %, based on total weight of the ready-to-use agent, of at least one toxicologically harmless co-bleach activator.

Considering the previously mentioned preferred embodiments, one quite specific and expressly preferred embodiment is when, in the method for bleaching keratinous fibers, the agents used contain in a cosmetic carrier, as a first component, at least one compound chosen from 4-acetyl-1-methylpyridinium p-toluenesulfonate, 4-acetyl-1-methylpyridinium benzenesulfonate, 4-acetyl-1-methylpyridinium bromide, 4-acetyl-1-methylpyridinium hydrogen sulfate, 4-acetyl-1-allylpyridinium p-toluenesulfonate, 4-acetyl-1-allylpyridinium benzenesulfonate, 4-acetyl-1-allylpyridinium bromide, 4-acetyl-1-allylpyridinium hydrogen sulfate, 4-acetyl-1-(2-hydroxyethyl)pyridinium p-toluenesulfonate, 4-acetyl-1-(2-hydroxyethyl)pyridinium benzenesulfonate, 4-acetyl-1-(2-hydroxyethyl)pyridinium bromide and 4-acetyl-1-(2-hydroxyethyl)pyridinium hydrogen sulfate; as a second component hydrogen peroxide in the preferred quantitative proportions already described; and, as an additional co-bleach activator component, at least one compound chosen from glycine, benzyl alcohol and Sodium Coceth-30 Sulfate.

Most particularly preferred are agents containing one of the following combinations, where weight percentages again relate to total weight of the ready-to-use agent:

Combination (a): 0.1 to 4.0 wt. % 4-acetyl-1-methylpyridinium p-toluenesulfonate, 0.1 to 3.0 wt. % glycine and 0.1 to 12.0 wt. % hydrogen peroxide.

Combination (b): 0.1 to 4.0 wt. % 4-acetyl-1-methylpyridinium p-toluenesulfonate, 0.1 to 3.0 wt. % benzyl alcohol and 0.1 to 12.0 wt. % hydrogen peroxide.

Combination (c): 0.1 to 4.0 wt. % 4-acetyl-1-methylpyridinium p-toluenesulfonate, 0.1 to 3.0 wt. % Sodium Coceth-30 Sulfate (active substance) and 0.1 to 12.0 wt. % hydrogen peroxide.

Among these, combination (a) mentioned above is most preferred.

One conventional route therefore consists in mixing, immediately before application, a first agent containing at least one cationic acyl pyridinium derivative of general formula (I) with a second agent in which the oxidizing agent(s) are contained.

The present invention therefore also provides a method for bleaching keratinous fibers, particularly human hair, wherein a bleaching agent is applied onto the keratin-containing fibers, left on the fibers for an exposure time of 1 to 30 minutes, and then rinsed out or washed out with a shampoo, wherein the bleaching agent is obtained immediately before application onto the hair by mixing a flowable preparation A containing the cationic acyl pyridinium derivatives of general formula (I), and an oxidizing agent preparation B containing at least one oxidizing agent chosen from hydrogen peroxide and/or the addition compounds thereof to organic or inorganic compounds.

Oxidizing agent preparation B is preferably an aqueous, flowable oxidizing agent preparation. Preferred agents according to the invention for bleaching keratinous fibers are those wherein the flowable oxidizing agent preparation B contains, based on its weight, 40 to 90 wt. %, preferably 50 to 85 wt. %, particularly preferably 55 to 80 wt. %, more preferably 60 to 77.5 wt. % and in particular 65 to 75 wt. % water.

Blonding processes on keratin fibers generally take place in an alkaline medium. To protect the keratin fibers and the skin as far as possible, it is not desirable to establish too high a pH. It is therefore preferred if the pH of the ready-to-use agent is from 7 to 11, particularly from 8 to 10.5. The pH values within the meaning of the present invention are pH values that have been measured at a temperature of 22° C.

Alkalizing agents that can be used according to the invention to establish the preferred pH can be chosen from ammonia, alkali metal hydroxides, alkanolamines, alkali metal metasilicates, alkali metal phosphates and alkali metal hydrogen phosphates.

Ready-to-use blonding agents comprising preparation A and oxidizing agent preparation B and optionally blonding preparation C should preferably have a pH in the range of 6 to 12. Application in an alkaline medium is particularly preferred. Application temperatures can be within a range of from 15 to 40° C. After an exposure period of 2 to 60, preferably 5 to 45 minutes, the blonding agent is removed from the hair by rinsing. There is no need for a secondary wash with a shampoo if a carrier containing a significant amount of surfactant was used.

Preferred blonding agents according to the invention for keratinous fibers have an alkaline pH. In another preferred embodiment, the ready-to-use agent has a pH of from 7.0 to 12.0, preferably from 8.0 to 11.0. The pH values within the meaning of the present invention are pH values that have been measured at a temperature of 22° C.

The pH is generally adjusted using pH regulators. To adjust the pH, the person skilled in the art is familiar with acidifying and alkalizing agents common in cosmetics. Alkalizing agents that can be used to adjust the pH are typically chosen from inorganic salts, particularly the alkali metals and alkaline earth metals, organic alkalizing agents, particularly amines, basic amino acids and alkanolamines, and ammonia. Preferred acidifying agents according to the invention are food acids such as citric acid, acetic acid, malic acid or tartaric acid, as well as dilute mineral acids. In the context of the investigations relating to the present invention, however, it has been shown that those which are preferred according to the invention additionally contain an inorganic alkalizing agent. The inorganic alkalizing agent according to the invention is preferably chosen from sodium hydroxide, potassium hydroxide, calcium hydroxide, barium hydroxide, sodium phosphate, potassium phosphate, sodium silicate, potassium silicate, sodium carbonate and potassium carbonate. Alkanolamines that can be used as alkalizing agents according to the invention are chosen from monoalkanolamines, dialkanolamines such as diethanolamine, or trialkanolamines such as triethanolamine. Preferred alkanolamines are chosen from 2-aminoethan-1-ol, 2-amino-2-methylpropan-1-ol and 2-amino-2-methylpropane-1,3-diol.

The sole use of hydrogen peroxide or the addition products thereof onto organic or inorganic compounds is often not sufficient for strong bleaching of very dark hair. In these cases, a combination of hydrogen peroxide and persulfates or peroxodisulfates is generally used. It has been shown that mixing acyl pyridinium derivatives of general structure (I) according to the invention and hydrogen peroxide results in an increase in bleaching power even in the case of a further combination of hydrogen peroxide and peroxomonosulfate salts or peroxodisulfate salts.

Should the consumer desire very strong blonding, it may therefore be preferred in a further embodiment if, in addition to the cationic acyl pyridinium compound of general structure (I) and hydrogen peroxide, at least one additional bleaching power enhancer is contained in the agent for bleaching keratinous fibers.

The additional bleaching power enhancer may already be incorporated into oxidizing agent preparation B. However, if the additional bleaching power enhancer is unstable when stored in aqueous solution or is not present in the oxidizing agent preparation B for other reasons, it may be preferred to mix a blonding preparation C, containing the additional bleaching power enhancer, into the bleaching agent consisting of preparation A and oxidizing agent preparation B immediately before application.

Within the framework of this invention, peroxo compounds and compounds that give aliphatic peroxocarboxylic acids and/or substituted perbenzoic acid under perhydrolysis conditions, carbonic acid derivatives, alkyl carbonates, alkyl carbamates, silyl carbonates and silyl carbamates can be used as additional bleaching power enhancers.

The bleaching power enhancer is preferably chosen from ammonium peroxodisulfate, alkali metal peroxodisulfates, ammonium peroxomonosulfate, alkali metal hydrogen peroxomonosulfates, alkali metal peroxodiphosphates and alkaline earth metal peroxides. Particularly preferred bleaching power enhancers are ammonium peroxodisulfate, potassium peroxodisulfate, sodium peroxodisulfate, potassium hydrogen peroxomonosulfate, potassium peroxodiphosphate, magnesium peroxide and barium peroxide. Particularly preferred according to the invention are agents having as bleaching power enhancer at least one inorganic salt chosen from peroxomonosulfates and/or peroxodisulfates. Furthermore, it has proved particularly preferable during work relating to the present invention if the agents contain at least two different peroxodisulfates. Preferred peroxodisulfate salts are combinations of ammonium peroxodisulfate and potassium peroxodisulfate and/or sodium peroxodisulfate. Peroxo compounds are contained in a quantity of 0.1 to 25 wt. %, particularly 0.5 to 15 wt. %, based on total weight of the ready-to-use agent. The persulfate salts or peroxodisulfate salts are generally used in the form of an optionally dedusted powder, paste or in the form of a pressed molding.

Anhydrous compositions according to the invention can contain an additional bleaching power enhancer instead of and/or as well as solid peroxo compounds.

As bleach enhancers it is possible to use compounds that give aliphatic peroxocarboxylic acids with preferably 1 to 10 C atoms, particularly 2 to 4 C atoms, and/or optionally substituted perbenzoic acid under perhydrolysis conditions. Suitable are substances that carry O- and/or N-acyl groups with the aforementioned number of C atoms and/or optionally substituted benzoyl groups. Preferred are polyacylated alkylenediamines, particularly tetraacetyl ethylenediamine (TAED), acylated triazine derivatives, particularly 1,5-diacetyl-2,4-dioxohexahydro-1,3,5-triazine (DADHT), acylated glycolurils, particularly tetraacetyl glycoluril (TAGU), N-acylimides, in particular N-nonanoyl succinimide (NOSI), acylated phenol sulfonates, particularly n-nonanoyl or isononanoyl oxybenzenesulfonate (n or i-NOBS), carboxylic anhydrides, particularly phthalic anhydride, acylated polyhydric alcohols, particularly triacetin, ethylene glycol diacetate and 2,5-diacetoxy-2,5-dihydrofuran.

As a bleach enhancer of the carbonic acid derivative type, it is preferred to use carbonate salts or hydrogen carbonate salts. These are preferably chosen from ammonium, alkali metal (particularly sodium and potassium) and alkaline earth metal (particularly magnesium and calcium) carbonate salts or hydrogen carbonate salts. Particularly preferred carbonate and hydrogen carbonate salts are ammonium hydrogen carbonate, ammonium carbonate, sodium hydrogen carbonate, sodium carbonate, potassium hydrogen carbonate, potassium carbonate, magnesium carbonate and calcium carbonate. These particularly preferred salts can be used either individually or in mixtures of at least two representatives thereof as bleach enhancers.

Bleach enhancers of the alkyl carbonates and carbamates type as well as silyl carbonates and silyl carbamates can be used as bleach enhancers in the anhydrous compositions and are characterized by compounds of the formula (BV)

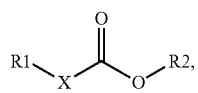

(BV)

wherein
R1 is a saturated or unsaturated, straight-chained, branched or cyclic, substituted or unsubstituted hydrocarbon residue, or a substituted or unsubstituted aryl group or a substituted or unsubstituted heterocycle,
X is a group O or NR3, where R3 is a hydrogen atom, a saturated or unsaturated, straight-chained, branched or cyclic, substituted or unsubstituted hydrocarbon residue or a substituted or unsubstituted silyl group or a substituted or unsubstituted aryl group or a substituted or unsubstituted heterocycle, and
R2 is a hydrogen atom, an alkali metal atom, in particular sodium, or a group $SiR_3$ in which the residues R independently of one another denote a hydrogen atom, a saturated or unsaturated, straight-chained, branched or cyclic, substituted or unsubstituted hydrocarbon residue or a trialkyl silyl group, preferably a trimethyl silyl group, or a substituted or unsubstituted aryl group or a substituted or unsubstituted heterocycle or a halogen or a substituted or unsubstituted hydroxy or amino group.

Compositions that are particularly preferably used according to the invention are characterized in that R1 in formula (BV) is chosen from methyl, ethyl, n-propyl, i-propyl, n-butyl, i-butyl, t-butyl and hydroxymethyl and hydroxyethyl. Preferred residues R2 and R3 in the formula (BV) are hydrogen, substituted or unsubstituted, straight-chained or branched alkyl residues and trialkyl silyl residues. Among these, hydrogen, methyl, ethyl, t-butyl and trimethyl silyl residues are preferred. Preferred residues R in the formula (BV) are substituted or unsubstituted, straight-chained or branched alkyl residues. Among these, the alkyl residues with 1 to 5 carbon atoms and the hydroxyalkyl residues are preferred, so that preferred compositions according to the invention are characterized in that the residues R in formula (BV) are chosen from methyl, ethyl, n-propyl, i-propyl, n-butyl, i-butyl, t-butyl and hydroxyethyl.

As other additional bleach enhancers, preferably at least one compound chosen from acetic acid, lactic acid, tartaric acid, citric acid, salicylic acid and ortho-phthalic acid can be contained in compositions according to the invention. The bleaching power enhancers used in addition to or instead of peroxo compounds are present in the cosmetic agents preferably in quantities of 0.05 to 10 wt. %, particularly in quantities of 0.2 to 5 wt. %, based on total weight of the ready-to-use agent.

Although in principle there are no restrictions in terms of the formulation of the blonding preparation C, it has proved preferable if preparation C is formulated in anhydrous form. Anhydrous within the meaning of the present invention means a water content, based on preparation C, of less than 5 wt. %, particularly less than 2 wt. %. Blonding preparations that contain less than 0.1 wt. % water may be most particularly preferred according to the invention. Preparation C is preferably formulated as a powder or as an anhydrous paste.

In its formulation as an anhydrous paste, it has proved to be particularly preferred if preparation C contains at least one non-hydroxylated fatty acid ester with a melting point of no more than 50° C., particularly no more than 30° C., and/or at least one $C_{10}$-$C_{30}$ fatty acid with at least one additional hydroxy group and/or derivative thereof. Esters of non-hydroxylated $C_6$-$C_{30}$ alkyl monocarboxylic acids with $C_2$-$C_{30}$ monoalcohols are preferably suitable according to the invention as fatty acid esters. Preferred are monoesters of fatty acids with monoalcohols having 2 to 24 C atoms. Preferred according to the invention are isopropyl myristate, isononanoic acid $C_{16-18}$ alkyl esters, 2-ethylhexyl palmitate, stearic acid 2-ethylhexyl ester, cetyl oleate, coconut fatty alcohol caprinate/caprylate, n-butyl stearate, oleyl erucate, isopropyl palmitate, oleyl oleate, lauric acid hexyl ester, myristyl myristate, cetearyl isononanoate and oleic acid decyl ester.

As has already been mentioned, agents used in the method according to the invention can be produced immediately before application from two or more separately packaged preparations. This is particularly appropriate for separating incompatible ingredients, thereby avoiding a premature reaction.

Persulfate salts or peroxodisulfate salts are generally used in the form of an optionally dedusted powder or in the form of a pressed molding. In order to avoid premature degradation of the acyl pyridinium derivatives according to the invention by contact with the persulfate or peroxodisulfates, it is preferred according to the invention if the persulfates or peroxodisulfates are packaged separately as component C.

The present invention also provides in this connection a method for bleaching human hair with an agent consisting of three components. This agent is produced immediately before application onto hair by carefully mixing a flowable preparation A containing cationic acyl pyridinium derivatives of general formula (I), an oxidizing agent preparation B containing at least one oxidizing agent chosen from hydrogen peroxide and/or the addition compounds thereof onto organic or inorganic compounds, and additionally a third preparation C present in powder form containing at least one inorganic persulfate salt or peroxodisulfate salt.

Mixing preparations A and B or, optionally, preparations A, B and C before application results in an application mixture which is an agent comprising the three essential ingredients.

An emulsifier or surfactant is preferably added to flowable preparations A and/or B. Surface-active substances are designated, depending on the area of application, as surfactants or emulsifiers and chosen from anionic, cationic, zwitterionic, amphoteric and nonionic surfactants and emulsifiers.

Anionic surfactants suitable in preparations according to the invention include any anionic surface-active substances suitable for use on the human body. These contain an anionic water-solubilizing group, such as a carboxylate, sulfate, sulfonate or phosphate group, and a lipophilic alkyl group with approximately 8 to 30 C atoms. The molecule may additionally contain glycol ether or polyglycol ether groups, ester, ether and amide groups and hydroxyl groups. Preferred anionic surfactants are alkyl sulfates, alkyl ether sulfates and ether carboxylic acids with 10 to 18 C atoms in the alkyl group and up to 12 glycol ether groups in the molecule.

Zwitterionic surfactants are those surface-active compounds having at least one quaternary ammonium group and at least one carboxylate, sulfonate or sulfate group in the molecule. Particularly suitable zwitterionic surfactants are the so-called betaines, such as N-alkyl N,N-dimethylammonium glycinates (e.g., cocoalkyl dimethylammonium glycinate), N-acylaminopropyl N,N-dimethylammonium glycinates (e.g., cocoacyl aminopropyl dimethylammonium glycinate), and 2-alkyl-3-carboxymethyl-3-hydroxyethyl imidazolines, each containing 8 to 18 C atoms in the alkyl or acyl group, and cocoacyl aminoethyl hydroxyethyl carboxymethyl glycinate. A preferred zwitterionic surfactant is the fatty acid amide derivative known by the INCI name Cocamidopropyl Betaine.

Amphoteric surfactants include surface-active compounds which, in addition to a $C_8$-$C_{24}$ alkyl or acyl group, contain at least one free amino group and at least one —COOH or —$SO_3H$ group in the molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case approximately 8 to 24 C atoms in the alkyl group. Particularly preferred amphoteric surfactants are N-cocoalkyl aminopropionate, cocoacyl aminoethyl aminopropionate and $C_{12}$-$C_{18}$ acyl sarcosine.

It has also proved advantageous if colorants according to the invention contain other, nonionogenic, surface-active substances. Nonionic surfactants contain as a hydrophilic group, for example, a polyol group, a polyalkylene glycol ether group or a combination of a polyol group and a polyalkylene glycol ether group. As nonionic surfactants, $C_8$-$C_{22}$ alkyl mono- and oligoglycosides and the ethoxylated analogs thereof are particularly suitable. In particular the non-ethoxylated compounds have proved particularly suitable. The alkylene oxide addition products onto saturated linear fatty alcohols and fatty acids with in each case 2 to 30 mol of ethylene oxide per mol of fatty alcohol or fatty acid have proved to be other preferred nonionic surfactants. Preparations having excellent properties are also obtained if they contain fatty acid esters of ethoxylated glycerol as the nonionic surfactants.

Anionic, nonionic, zwitterionic or amphoteric surfactants are used in amounts of 0.1 to 45 wt. %, preferably 1 to 30 wt. % and most particularly preferably 1 to 15 wt. %, based on total amount of the ready-to-use agent.

According to the invention, preference is likewise given to cationic surfactants of the quaternary ammonium compound, ester quat and amidoamine types. Preferred quaternary ammonium compounds are ammonium halides, particularly chlorides and bromides such as alkyl trimethylammonium chlorides, dialkyl dimethylammonium chlorides and trialkyl methylammonium chlorides, and the imidazolium compounds known under the INCI names Quaternium-27 and Quaternium-83. The long alkyl chains of the above-mentioned surfactants preferably comprise 10 to 18 carbon atoms.

Quaternized protein hydrolyzates are further cationic surfactants that can be used according to the invention. Alkyl amidoamines are conventionally produced by amidating natural or synthetic fatty acids and fatty acid cuts with dialkyl aminoamines. A particularly suitable compound according to the invention from this group of substances is the stearamidopropyl dimethylamine commercially available with the name Tegoamid S 18. Ester quats are known substances which contain both at least one ester function and at least one quaternary ammonium group as structural elements. Preferred ester quats include quaternized ester salts of fatty acids with triethanolamine, quaternized ester salts of fatty acids with diethanol alkylamines and quaternized ester salts of fatty acids with 1,2-dihydroxypropyl dialkylamines. Such products are marketed, for example, with the trade marks Stepantex, Dehyquart and Armocare.

Agents used according to the invention preferably contain cationic surfactants in amounts of 0.05 to 10 wt. %, based on total agent. Quantities of 0.1 to 5 wt. % are particularly preferred.

In one preferred embodiment, nonionic, zwitterionic and/or amphoteric surfactants and mixtures thereof may be preferred.

In addition, it has proved advantageous if the oxidizing agent preparations contain at least one stabilizer or complexing agent. Particularly preferred stabilizers are phenacetin, alkali benzoates (sodium benzoate) and salicylic acid. Use of so-called complexing agents is also preferred according to the invention. Complexing agents are substances capable of complexing metal ions. Preferred complexing agents are so-called chelating agents (i.e., substances which form cyclic compounds with metal ions, one individual ligand having more than one coordination site on a central atom, that is, being at least "bidentate"). The number of bound ligands depends on the coordination number of the central ion. Preferred complexing agents according to the invention are nitrogen-containing polycarboxylic acids, particularly EDTA, and phosphonates, preferably hydroxyalkane or aminoalkane phosphonates and particularly 1-hydroxyethane 1,1-diphosphonate (HEDP) or the di- or tetrasodium salt thereof and/or ethylenediamine tetramethylene phosphonate (EDTMP) or the hexasodium salt thereof and/or diethylenetriamine pentamethylene phosphonate (DTPMP) or the hepta- or octasodium salt thereof.

Preferably, the agent contains at least one thickener. There are no restrictions in principle concerning these thickeners. Both organic and purely inorganic thickeners can be used.

As previously mentioned, agents according to the invention can be in the form of pure bleaching agents (i.e., so-called blonding agents), as well as dyeing and bleaching agents that also effect dyeing of the keratin fibers simultaneously with the bleaching.

Depending on the requirements placed on the dyed color, the person skilled in the art is aware of various dyeing systems for providing color-modifying cosmetics, particularly for skin or keratin-containing fibers such as human hair. So-called oxidation dye preparations are used for permanent, high-intensity dyed colors with corresponding fastness characteristics. Such dyes conventionally contain oxidation dye precursors, so-called developer components and coupler components. Under the influence of oxidizing agents or atmospheric oxygen, developer components develop the actual dyes through action with one another or by coupling with one or more coupler components. Oxidation dye preparations are distinguished by excellent, long-lasting dyeing results. A mixture of a relatively large number of oxidation dye precursors must, however, normally be used if natural-looking dyed colors are to be obtained; in many cases, direct dyes are additionally used for shading purposes. For temporary dyeing, dyes or tints containing so-called direct dyes as the coloring component are conventionally used. These are dye molecules which key directly to the substrate and do not need an oxidative process to develop the color. These dyes include for example henna, which has been known since antiquity for dyeing bodies and hair. These dyed colors are in general distinctly more sensitive to shampooing than are oxidatively dyed colors, such that an often unwanted shift in shade or even a visible, uniform color loss then occurs very much more quickly.

In one embodiment for color modification, the subject matter of the present invention may be combined with at least one color-modifying component. Color-modifying components are preferably chosen from (1) at least one oxidation dye precursor and/or (2) at least one direct dye.

Oxidation dyes contain at least one developer component and optionally at least one coupler component. Coupler and developer components are also known as oxidation dye precursors. Oxidation dye preparations may also additionally contain direct dyes as shading agents. Preferred agents for dyeing and/or bleaching keratinous fibers contain at least one oxidation dye precursor of the developer and coupler type. The coloring component can be incorporated into preparation A, oxidizing agent preparation B or optionally blonding preparation C. The coloring component is preferably incorporated into the emulsion preparation A.

Color-modifying agents are often used in bleaching agents to achieve a matting effect. The person skilled in the art understands the term matting to mean the ability of an agent to compensate for yellow or red impressions remaining in the fiber during bleaching by means of complementary hair colors. Relatively small amounts of coloring components are often used for this purpose, preferably less than 1.0 wt. %, particularly preferably less than 0.5 wt. % of all coloring components, based on total weight of the agent according to the invention. Preferred agents for bleaching keratinous fibers contain at least one oxidation dye precursor of the developer type and/or coupler type.

Bleaching agents according to the invention contain as oxidation dye precursors at least one coupler component and at least one developer component. Preferred developer components are chosen from at least one compound from p-phenylenediamine, p-tolylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis(2-hydroxyethyl)-N,N'-bis(4-aminophenyl)-1,3-diaminopropan-2-ol, bis(2-hydroxy-5-aminophenyl)methane, 1,3-bis(2,5-diaminophenoxy)propan-2-ol, N,N'-bis(4-aminophenyl)-1,4-diazacycloheptane, 1,10-bis(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine and the physiologically acceptable salts thereof. Particularly preferred developer components are p-tolylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and the physiologically acceptable salts thereof. The developer components are preferably used in an amount of 0.0001 to 0.5 wt. %, preferably 0.001 to 0.2 wt. %, based on ready-to-use matting bleaching agent.

In the context of oxidative dyeing, coupler components alone do not form any significant dyed color but additionally require the presence of developer components. It is therefore preferred according to the invention that, when at least one coupler component is used, at least one developer component is also used. Preferred coupler components include 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts of the above compounds. Resorcinol, 2-methylresorcinol, 5-amino-2-methylphenol, 3-aminophenol, 2-(2,4-diaminophenoxy)ethanol, 1,3-bis(2,4-diaminophenoxy)propane, 1-methoxy-2-amino-4-(2'-hydroxyethylamino)benzene, 2-amino-3-hydroxypyridine and 1-naphthol and one of the physiologically acceptable salts thereof are particularly preferred. The coupler components are preferably used in an amount of 0.0001 to 0.5 wt. %, preferably 0.001 to 0.2 wt. %, based on the ready-to-use matting bleaching agent.

Agents according to the invention can also contain at least one direct dye. These are dyes which key directly to the hair and do not need an oxidative process to develop the color. Typical direct dyes are nitrophenylenediamines, nitroaminophenols, azo dyes, anthraquinones or indophenols. Direct dyes may be subdivided into anionic, cationic and nonionic direct dyes. Direct dyes are each preferably used in an amount of 0.001 to 0.2 wt. %, preferably 0.001 to 0.1 wt. %, based on the entire ready-to-use preparation. Total amount of direct dyes is preferably no more than 0.1 wt. %.

Preferred anionic direct dyes are compounds known by the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenol blue. Preferred cationic direct dyes here are cationic triphenylmethane dyes (such as Basic Blue 7, Basic Blue 26, Basic Violet 2 and Basic Violet 14), aromatic systems which are substituted with a quaternary nitrogen group (such as Basic Yellow 57, Basic Red 76, Basic Blue 99, Basic Brown 16 and Basic Brown 17), and direct dyes containing a heterocycle having at least one quaternary nitrogen atom, as are mentioned, for example, in claims 6 to 11 of EP-A2-998 908. Compounds also known by the names Basic Yellow 87, Basic Orange 31 and Basic Red 51 are most particularly preferred cationic direct dyes. Cationic direct dyes distributed under the trademark Arianor are likewise most particularly preferred cationic direct dyes according to the invention. Suitable nonionic direct dyes include nonionic nitro and quinone dyes and neutral azo dyes. Preferred nonionic direct dyes include compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

It is not necessary for the optionally contained direct dyes each to be uniform compounds. Instead, as a result of the production processes for the individual dyes, subordinate quantities of still further components may be present, provided that these do not have a disadvantageous effect on the dyeing result or have to be excluded for other, for example toxicological, reasons. Naturally occurring dyes may furthermore also be used as direct dyes, such as are present in henna red, henna neutral, henna black, chamomile flowers, sandalwood, black tea, walnut, alder buckthorn bark, sage, logwood, madder root, catechu and alkanet root.

In one preferred embodiment of the present invention, the agent contains a coloring matting combination comprising a combination of at least one blue direct dye and one red direct dye, the weight ratio between the sum of all the blue direct dyes and the sum of all the red direct dyes having a value greater than or equal to 1. This avoids undesirable color shifts towards rosy/pink shades.

Preferred agents according to the invention are those wherein the total weight of all blue direct dyes is greater than the total weight of all red direct dyes. Preferred dye combinations according to the invention are those having at least the combination of tetrabromophenol blue and Acid Red 92; tetrabromophenol blue and Acid Red 98; tetrabromophenol blue and Acid Red 94; tetrabromophenol blue and Acid Red 87 or tetrabromophenol blue and Acid Red 51.

In addition, it may be preferred if the agent contains further direct dyes. The agent particularly preferably contains as a further direct dye a yellow and/or orange dye. This is advantageous in particular if undesired reddish color shifts occur during the blonding process.

Furthermore, agents according to the invention can contain additional active substances, auxiliary substances and additives, such as nonionic polymers (such as vinylpyrrolidinone/vinyl acrylate copolymers, polyvinylpyrrolidinone and vinylpyrrolidinone/vinyl acetate copolymers, polyethylene glycols and polysiloxanes); cationic polymers (such as quaternized cellulose ethers, polysiloxanes with quaternary groups, dimethyl diallyl ammonium chloride polymers, acrylamide-dimethyl diallyl ammonium chloride copolymers, dimethylaminoethyl methacrylate/vinylpyrrolidinone copolymers quaternized with diethyl sulfate, vinylpyrrolidinone-imidazolinium methochloride copolymers and quaternized polyvinyl alcohol); zwitterionic and amphoteric polymers (such as acrylamidopropyl-trimethylammonium chloride/acrylate copolymers and octylacrylamide/methyl methacrylate/t-butylaminoethyl methacrylate/2-hydroxypropyl methacrylate copolymers); anionic polymers (such as polyacrylic acids, crosslinked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-t-butylacrylamide terpolymers); further thickeners (such as agar-agar, guar gum, alginates, gum arabic, gum karaya, locust bean gum, linseed gum, dextrans, cellulose derivatives, e.g. methyl cellulose, hydroxyalkyl cellulose and carboxymethyl cellulose, starch fractions and derivatives such as amylose, amylopectin and dextrins, clays such as bentonite or synthetic hydrocolloids such as polyvinyl alcohol); structurants (such as glucose, maleic acid and lactic acid); hair-conditioning compounds (such as phospholipids, soy lecithin, egg lecithin and cephalins, as well as silicone oils); protein hydrolyzates (particularly elastin, collagen, keratin, milk protein, soy protein and wheat protein hydrolyzates, the condensation products thereof with fatty acids and quaternized protein hydrolyzates); perfume oils; cyclodextrins; active substances that improve fiber structure (particularly mono-, di- and oligosaccharides such as glucose, galactose, fructose, fruit sugar and lactose); defoamers (such as silicones, preferably dimethicone); dyes for tinting the agent; anti-dandruff active substances (such as piroctone olamine, zinc omadine and climbazole); light stabilizers or UV blockers (particularly derivatized benzophenones, cinnamic acid derivatives and triazine); active substances (such as panthenol, pantothenic acid, pantolactone, allantoin, pyrrolidinone carboxylic acids and the salts thereof and bisabolol); vitamins, provitamins and vitamin precursors (particularly those from groups A, $B_3$, $B_5$, $B_6$, C, E, F and H); cholesterol; consistency enhancers (such as sugar esters, polyol esters or polyol alkyl ethers); fats and waxes (such as beeswax, montan wax and paraffins); fatty acid alkanolamides; swelling and penetrating agents (such as glycerol, propylene glycol monoethyl ether, carbonates, hydrogen carbonates, guanidines, ureas and primary, secondary and tertiary phosphates); opacifiers (such as latex, styrene/PVP and styrene/acrylamide copolymers); pearlescent agents (such as ethylene glycol mono- and distearate and PEG-3 distearate); pigments; propellants (such as propane-butane mixtures, $N_2O$, dimethyl ether, $CO_2$ and air) and antioxidants.

One skilled in the art selects these additional substances based on the desired properties of the agents. Concerning further optional components and the amounts of these components used, express reference is made to the relevant handbooks known to the person skilled in the art, for example, Kh. Schrader, Grundlagen and Rezepturen der Kosmetika, 2nd Ed., Hüthig Buch Verlag, Heidelberg, 1989.

Compositions according to the invention may contain as a further component at least one ammonium compound from the group ammonium chloride, ammonium carbonate, ammonium bicarbonate, ammonium sulfate and/or ammonium carbamate in an amount of 0.5 to 10, preferably 1 to 5 wt. %, based on total composition of the agent.

The agents contain the active substances in a cosmetic carrier. This cosmetic carrier is preferably aqueous, alcoholic or aqueous-alcoholic. Carriers suitable for the purpose of hair bleaching are, for example, creams, emulsions, gels or surfactant-containing foaming solutions, such as shampoos, foam aerosols or other preparations suitable for use on hair. It is, however, also possible to provide for storage a formulation in powdered or tablet form, which is preferred for bleaching agents. Prior to application, this is then mixed in a solvent such as water, or with organic solvents or mixtures of water and organic solvents, to obtain the application mixture. An aqueous carrier contains for the purposes of the invention at least 40 wt. %, particularly at least 50 wt. %, water. For the purposes of the present invention, aqueous-alcoholic solutions refer to aqueous solutions containing 3 to 70 wt. % of a $C_1$-$C_4$ alcohol, particularly ethanol or isopropanol. Agents according to the invention may additionally contain further organic solvents such as methoxybutanol, ethyl diglycol, 1,2-propylene glycol, n-propanol, n-butanol, n-butylene glycol, glycerol, diethylene glycol monoethyl ether and diethylene glycol mono-n-butyl ether. All water-soluble organic solvents are preferred for this purpose. Preferred agents additionally contain a non-aqueous solvent, with particularly preferred agents containing the solvent in a concentration of 0.1 to 30 wt. %, preferably in a concentration of 1 to 20 wt. %, most particularly preferably in a concentration of 2 to 10 wt. %, based on total weight of the agent.

In the method according to the invention for bleaching keratinous fibers, a bleaching agent according to the above features is applied onto the keratin-containing fibers, left on the fiber for an exposure time of 1 to 30 minutes and then rinsed out again or washed out with a shampoo. Preferably, the agent is left on the hair for an exposure time of 1 to 30 minutes, preferably 5 to 30 minutes and particularly preferably 10 to 30 minutes. Preferably the temperature during the exposure time is from 10° C. to 40° C., particularly from 20° C. to 38° C. and particularly preferably from 25° C. to 35° C. The methods according to the invention achieve excellent bleaching results even at physiologically acceptable temperatures of below 45° C. They are therefore particularly suitable for dyeing human hair.

During the exposure time of the agent on the fiber, it may be advantageous to support the bleaching process by adding heat. Heat can be added by an external heat source such as hot air from a hot air blower and, particularly when dyeing hair on a living subject, by the subject's body heat. In the latter case, the section to be dyed is generally covered with a hood.

After the exposure time, the hair dye is removed from the hair being dyed by rinsing it out, optionally with the aid of a shampoo. There is no need for a secondary wash with a shampoo if a carrier containing a significant amount of surfactant (e.g., a coloring shampoo) was used.

Bleaching agents can therefore be formulated as one-component agents, as two-component agents, and used accordingly. Separation into multi-component systems can be considered, particularly where incompatibilities of the ingredients are to be expected or feared. In such systems, the agent used is prepared by the consumer by mixing the components directly before application.

A preferred bleaching method is one in which compounds of the general structure (I) are initially present separately from hydrogen peroxide. The present invention accordingly also provides a method for bleaching and optionally dyeing human hair, wherein a water-based composition containing hydrogen peroxide is mixed with a composition containing at least one compound of general structure (I) (see above) to form a bleaching agent, and the latter is applied onto the hair.

The present application secondly provides an agent for bleaching keratinous fibers, containing in a cosmetic carrier (i) at least one cationic acyl pyridinium derivative of formula (I)

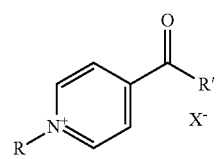

wherein
R is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a heteroaryl $C_1$-$C_6$ alkyl group, a mono- or di-$C_1$-$C_6$-alkylamino $C_2$-$C_6$ alkyl group, a 3-oxobutyl group, a 2-oxopropyl group, an aryl group or a heteroaryl group,
R' is a $C_1$-$C_4$ alkyl group, a $C_2$-$C_6$ hydroxyalkyl group or a $C_1$-$C_6$ alkoxy $C_2$-$C_6$ alkyl group
$X^-$ is a physiologically acceptable anion,
(ii) at least one associative polymer, and
(iii) hydrogen peroxide.

One preferred embodiment of the second subject matter of the invention is an agent which additionally contains at least one dialkyl ether and/or dialkyl carbonate. Another, particularly preferred embodiment of the present invention exists if the bleaching agent additionally contains at least one co-bleach activator and/or the physiologically acceptable salt thereof. With regard to other preferred embodiments of the agent according to the invention, the statements relating to the method according to the invention apply mutatis mutandis.

The present invention also provides the cosmetic, non-therapeutic use of an agent of the second subject matter of the invention for bleaching keratinous fibers, particularly human hair, with reduced fiber damage.

The present invention also provides the cosmetic, non-therapeutic use of an agent of the second subject matter of the invention to improve the condition of fibers during the bleaching process.

A reduction in fiber damage and an improvement in condition can be quantified based on split ends and hair breakage that occurs during the bleaching process. One preferred embodiment of the present invention is therefore the cosmetic, non-therapeutic use of an agent of the second subject matter of the invention for the simultaneous reduction in split ends of the fibers and/or for the simultaneous reduction of hair breakage during the bleaching process.

With regard to other preferred embodiments of the use according to the invention, the statements relating to the method according to the invention apply mutatis mutandis. The following examples are intended to explain the present invention without limiting it or restricting it to the examples.

EXAMPLES 1.1 Preparation of Blonding Creams
Blonding creams were prepared as follows from the components listed below.

|  | wt. % | | |
| --- | --- | --- | --- |
| Raw material | C1 | C2 | E1 |
| Hydrenol D | 12.0 | 12.0 | 12.0 |
| Lorol tech. | 2.4 | 2.4 | 2.4 |
| Texapon NSO | 26.5 | 26.5 | 26.5 |
| Stabylen 30 | 0.1 | 0.1 | 0.1 |

-continued

| Raw material | wt. % | | |
|---|---|---|---|
| | C1 | C2 | E1 |
| Cetiol OE | 2.4 | 2.4 | 2.4 |
| Turpinal SL | 0.2 | 0.2 | 0.2 |
| Sodium silicate 40/42 | 0.5 | 0.5 | 0.5 |
| Gluadin W 40 | 0.35 | 0.35 | 0.35 |
| Ammonium sulfate | 1.0 | 1.0 | 1.0 |
| Ammonia 25 wt. % aqueous | 7.6 | 7.6 | 7.6 |
| 4-Acetyl-1-methylpyridmium p-toluenesulfonate | — | — | 2.0 |
| Glycine | — | — | 2.0 |
| Ammonium hydrogen carbonate | — | 4.0 | — |
| Water | to 100 | to 100 | to 100 |

Raw materials: Hydrenol D (INCI name: Cetearyl alcohol; Cognis); Lorol tech. (INCI name: Coconut alcohol; Cognis); Texapon NSO (approx. 27.5% active substance; INCI name: Sodium Laureth Sulfate; Cognis); Stabylen 30 (INCI name: Acrylates/Vinylisodecanoate Crosspolymer; Sigma); Cetiol OE (INCI name: Dicarylylether; Cognis); Turpinal SL (approx. 60% active substance content; INCI name: Etidronic Acid, Aqua; Solutia); Gluadin W 40 (approx. 42% active substance; INCI name: hydrolyzed wheat protein; Cognis).

Stabylen 30 and Cetiol OE were predispersed at room temperature. Next, the other components were incorporated in succession with stirring, and the mixture was then topped off with water and the formulation was stirred cold. Formulations C1 and C2 are comparative formulations which are not according to the invention, without a bleach activator system and with a bleach activator according to WO2006036747 respectively. Formulation E1 is an example according to the invention with the bleach activator 4-acetyl-1-methylpyridinium p-toluenesulfonate and glycine as a bleach activator system.

Each blonding cream was thoroughly mixed in a 1:1 ratio with a developer dispersion of the following composition. The pH value of the application mixture was from 9 to 10.2.

| Raw material | wt. % |
|---|---|
| Ammonia, 25% | 0.62 |
| Dipicolic acid | 0.10 |
| Disodium pyrophosphate | 0.03 |
| Turpinal SL | 1.50 |
| Texapon NSO | 2.00 |
| Dow Corning DB 110 A | 0.07 |
| Aculyn 33A (acrylic polymer) | 12.00 |
| Hydrogen peroxide 50% | 22.40 |
| Water | to 100 |

Raw materials: Texapon NSO (approx. 27.5%; INCI name: Sodium Laureth Sulfate; Cognis); Aculyn 33 (approx. 28%; INCI name: Acrylates Copolymer; Rohm & Haas); DC DB 110 A (INCI name: Dimethicon; Dow Corning).

For the blonding process, strands of light brown hair (Codes: Kerling 6/0) with a weight of approx. 0.7 g, had 4 times the amount of the finished application mixture applied to them. After blonding the strands for 30 min at 32° C., they were washed with a conventional commercial shampoo and dried with a hairdryer. The strands were then stored for 24 h at 25° C. and 25% relative humidity.

2. Measurement of Hair Damage

Untreated control strands and the strands treated with the bleaching agents were combed 20,000 times using plastic combs from Hercules Sagemann. During this operation the strands were regularly discharged. The temperature was 25° C. and the relative humidity 25%.

Determination of the Rate of Split Ends

Tips with a length of 1.5 cm each were cut off the hair strands and transferred onto a very fine sieve (diameter 200 μm). Using a stream of air generated from below, hair with split ends was separated from unsplit hair. For each strand, the amount of hair with split ends remaining on the sieve was determined and compared with the total amount of the cut hair.

Determination of Hair Breakage

For each strand the broken hair was collected in a device below the comb, weighed and compared with the total amount of hair in each strand.

3. Results

TABLE 1

Rate of Split Ends

| Hair sample | Proportion of split ends after 20,000 combing strokes in [%] | Difference compared with untreated hair sample in [%] |
|---|---|---|
| Kerling 6/0, untreated | 18 | — |
| Bleached with C1 + developer dispersion | 13 | +26 |
| Bleached with C2 + developer dispersion | 24 | −35 |
| Bleached with E1 + developer dispersion | 3 | +86 |

TABLE 2

Hair Breakage

| Hair sample | Proportion of hair breakage after 20,000 combing strokes in [%] | Difference compared with untreated hair sample in [%] |
|---|---|---|
| Kerling 6/0, untreated | 7 | — |
| Bleached with C1 + developer dispersion | 9 | −32 |
| Bleached with C2 + developer dispersion | 13 | −88 |
| Bleached with E1 + developer dispersion | 1 | +89 |

3.1 Interpretation of Results

The bleaching formulation according to the invention (E1+ developer dispersion) leads to a significant improvement in split ends and hair breakage compared with untreated hair as well as with the comparative formulation without cationic acyl pyridinium compound according to the invention (C1+ developer dispersion).

We claim:

1. Method for bleaching keratinous fibers comprising:
applying a bleaching agent onto keratin-containing fibers,
leaving the agent on the fibers for a time of 1 to 30 minutes, and
rinsing out the agent or washing out the agent with a shampoo,
wherein the bleaching agent comprises in a cosmetic carrier hydrogen peroxide,
at least one cationic acyl pyridinium derivative of formula (I)

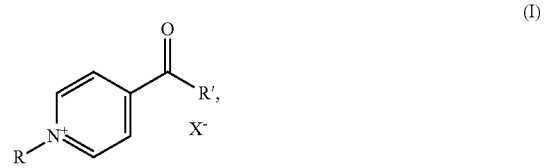

(I)

wherein
R is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a $C_1$-$C_6$ dialkylamino $C_2$-$C_6$ alkyl group, a heteroaryl $C_1$-$C_6$ alkyl group, a 3-oxobutyl group, a 2-oxopropyl group, an aryl group or a heteroaryl group, R' is a $C_1$-$C_4$ alkyl group, a $C_2$-$C_6$ hydroxyalkyl group or a $C_1$-$C_6$ alkoxy $C_2$-$C_6$ alkyl group, and $X^-$ is a physiologically acceptable anion, at least one associative polymer and at least one co-bleach activator and/or the physiologically acceptable salt thereof.

2. Method according to claim 1, wherein R is a $C_1$-$C_6$ alkyl group, a $C_2$-$C_6$ alkenyl group or a $C_2$-$C_6$ hydroxyalkyl group.

3. Method according to claim 1, wherein the at least one cationic acyl pyridinium derivative according to formula (I) is chosen from at least one compound from the group of 4-acetyl-1-methylpyridinium p-toluenesulfonate, 4-acetyl-1-methylpyridinium benzenesulfonate, 4-acetyl-1-methylpyridinium bromide, 4-acetyl-1-methylpyridinium hydrogen sulfate, 4-acetyl-1-allylpyridinium p-toluenesulfonate, 4-acetyl-1-allylpyridinium benzenesulfonate, 4-acetyl-1-allylpyridinium bromide, 4-acetyl-1-allylpyridinium hydrogen sulfate, 4-acetyl-1-(2-hydroxyethyl)pyridinium p-toluenesulfonate, 4-acetyl-1-(2-hydroxyethyl)pyridinium benzenesulfonate, 4-acetyl-1-(2-hydroxyethy)pyridinium bromide, and 4-acetyl-1-(2-hydroxyethy)pyridinium hydrogen sulfate.

4. Method according to claim 1, wherein the bleaching agent further comprises at least one dialkyl ether and/or dialkyl carbonate.

5. Method according to claim 1, wherein the co-bleach activator and/or physiologically acceptable salt thereof is at least one co-bleach activator according to formula (II) and/or the physiologically acceptable salt thereof

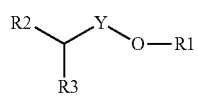
(II)

wherein
Y is a carbonyl group, a direct bond or methylene group;
R1 is hydrogen, a $C_1$-$C_4$ alkyl group, a physiologically acceptable cation or an $SO_3^-$ or a $PO_3^{2-}$ group;
R2 is an amino group, a methylamino group, a dimethylamino group, a trimethylammonio group, phenyl, benzyl, phenoxymethyl, 1-naphthyl, 2-naphthyl, 2-, 3-, 4-toluoyl, or an R4-O—(CH$_2$CH$_2$O)$_n$ group, wherein R4 is a $C_6$-$C_{20}$ alkyl group and n is a number greater than 14;
R3 is hydrogen or an optionally branched $C_1$-$C_6$ alkyl group;

with the proviso that
if Y is a carbonyl group,
R1 is hydrogen, a $C_1$-$C_4$ alkyl group or a physiologically acceptable cation,
R2 is an amino group, a methylamino group, a dimethylamino group or a trimethylammonio group, and
R3 is hydrogen or an optionally branched $C_1$-$C_6$ alkyl group,
if Y is a direct bond,
R1 is hydrogen,
R2 is phenyl, benzyl, phenoxymethyl, 1-naphthyl, 2-naphthyl, 2-, 3- or 4-toluoyl, and
R3 is hydrogen or an optionally branched $C_1$-$C_6$ alkyl group,
and if Y is a methylene group,
R1 is an $SO_3^-$ or a $PO_3^{2-}$ group,
R2 is an R4-O(CH$_2$CH$_2$O)$_n$ group, wherein R4 is a $C_6$-$C_{20}$ alkyl group and n is a number greater than 14, and
R3 is hydrogen.

6. Method according to claim 1, wherein the at least one co-bleach activator and/or physiologically acceptable salt thereof is at least glycine.

7. Agent for bleaching keratinous fibers comprising in a cosmetic carrier:
(i) at least one cationic acyl pyridinium derivative of formula (I)

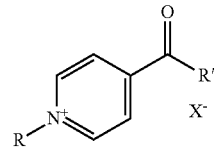
(I)

where
R is a $C_1$-$C_6$ alkyl group, a $C_2$-$C_6$ alkenyl group, a $C_2$-$C_6$ hydroxyalkyl group, a $C_1$-$C_6$ alkoxy $C_2$-$C_6$ alkyl group, a carboxy $C_1$-$C_6$ alkyl group, an aryl $C_1$-$C_6$ alkyl group, a heteroaryl $C_1$-$C_6$ alkyl group, a mono- or di-$C_1$-$C_6$-alkylamino $C_2$-$C_6$ alkyl group, a 3-oxobutyl group, a 2-oxopropyl group, an aryl group or a heteroaryl group,
R' is a $C_1$-$C_4$ alkyl group, a $C_2$-$C_6$ hydroxyalkyl group or a $C_1$-$C_6$ alkoxy $C_2$-$C_6$ alkyl group, and
$X^-$ is a physiologically acceptable anion,
(ii) at least one associative polymer,
(iii) hydrogen peroxide, and
(iv) at least one co-bleach activator and/or the physiologically acceptable salt thereof.

8. Agent according to claim 7 further comprising at least one dialkyl ether and/or dialkyl carbonate.

* * * * *